United States Patent
Diaz De Rienzo et al.

(10) Patent No.: US 10,674,726 B2
(45) Date of Patent: Jun. 9, 2020

(54) COMPOSITION

(71) Applicant: Conopco, Inc., Englewood Cliffs, NJ (US)

(72) Inventors: Mayri Alejandra Diaz De Rienzo, Manchester (GB); Andrew Stephen Jamieson, Cheshire (GB); Paul Simon Stevenson, Liverpool (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/103,128

(22) PCT Filed: Dec. 16, 2014

(86) PCT No.: PCT/EP2014/077928
§ 371 (c)(1),
(2) Date: Jun. 9, 2016

(87) PCT Pub. No.: WO2015/091457
PCT Pub. Date: Jun. 25, 2015

(65) Prior Publication Data
US 2016/0309715 A1  Oct. 27, 2016

(30) Foreign Application Priority Data
Dec. 19, 2013 (EP) .................................... 13198649

(51) Int. Cl.
| | | |
|---|---|---|
| *A61K 8/00* | (2006.01) |
| *A61K 8/18* | (2006.01) |
| *A61Q 15/00* | (2006.01) |
| *A01N 43/16* | (2006.01) |
| *C11D 1/04* | (2006.01) |
| *C11D 3/20* | (2006.01) |
| *C11D 3/48* | (2006.01) |
| *A01N 37/02* | (2006.01) |
| *A61K 8/36* | (2006.01) |
| *A61K 8/60* | (2006.01) |
| *A61Q 5/02* | (2006.01) |
| *A61Q 5/12* | (2006.01) |
| *A61Q 19/10* | (2006.01) |

(52) U.S. Cl.
CPC ............ *A01N 43/16* (2013.01); *A01N 37/02* (2013.01); *A61K 8/36* (2013.01); *A61K 8/602* (2013.01); *A61Q 5/02* (2013.01); *A61Q 5/12* (2013.01); *A61Q 15/00* (2013.01); *A61Q 19/10* (2013.01); *C11D 1/04* (2013.01); *C11D 3/2075* (2013.01); *C11D 3/48* (2013.01)

(58) Field of Classification Search
CPC ...................................................... A01N 43/16
See application file for complete search history.

(56) References Cited

U.S. PATENT DOCUMENTS

| | | | |
|---|---|---|---|
| 5,091,101 A | * | 2/1992 | Hildreth ............... C11D 10/045 510/337 |
| 5,767,090 A | | 6/1998 | Stanghellini et al. |
| 2007/0191292 A1 | | 8/2007 | Gandhi et al. |
| 2010/0272690 A1 | | 10/2010 | Gandhi et al. |
| 2014/0349902 A1 | | 11/2014 | Allef et al. |

FOREIGN PATENT DOCUMENTS

| | | |
|---|---|---|
| CN | 103146496 | 6/2013 |
| DE | 102011090030 | 7/2013 |
| EP | 0499434 | 8/1992 |
| EP | 2410039 | 1/2012 |
| EP | 2410039 A1 * | 1/2012 |
| JP | 2005530857 | 10/2005 |
| WO | WO9504459 | 2/1995 |
| WO | WO0250225 | 6/2002 |
| WO | WO2004000016 | 12/2003 |
| WO | WO2007095258 | 1/2008 |
| WO | WO2008013899 | 1/2008 |
| WO | WO2009072097 | 6/2009 |
| WO | WO 2012/010407 A1 * | 1/2012 |
| WO | WO2012010406 | 1/2012 |

OTHER PUBLICATIONS

Search Report EP13198649, dated May 15, 2014.
Written Opinion EP13198649, dated May 15, 2014.
IPRP2 in PCTEP2014077928, dated Apr. 19, 2016.
Search Report in PCTEP2014077928, dated Mar. 17, 2015.
Written Opinion 1 in PCTEP2014077928, dated Mar. 17, 2015.
Written Opinion 2 in PCTEP2014077928, dated Nov. 19, 2015.

* cited by examiner

*Primary Examiner* — David Browe
(74) *Attorney, Agent, or Firm* — Foley & Lardner LLP

(57) ABSTRACT

An antimicrobial composition that includes a rhamnolipid and a cell membrane disruptor, wherein the cell membrane disruptor includes a carboxylic acid selected from the group consisting of caprylic acid, azelaic acid, caproic acid, malic acid, maleic acid, fumaric acid, succinic acid, glutaric acid, adipic acid, tartaric acid, and mixtures thereof, and wherein the cell membrane disruptor is present in the range of 0.01-10 wt % of the composition.

9 Claims, 1 Drawing Sheet

BEFORE TREATMENT
AFTER TREATMENT
A
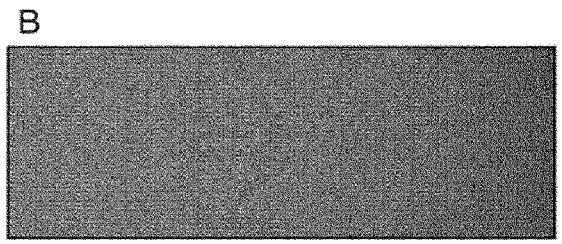
B
C
D
E
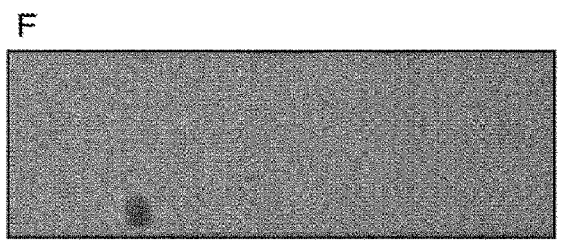
F
G
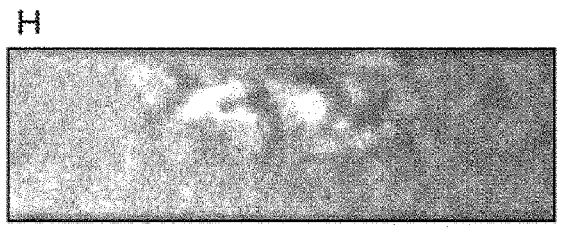
H

COMPOSITION

The present invention relates to an improved bactericidal composition comprising a rhamnolipid.

Despite the prior art there remains a need for improved bactericidal rhamnolipid compositions.

Accordingly, and in a first aspect, the present invention provides a bactericidal composition comprising a rhamnolipid and a cell membrane disrupter.

BRIEF DESCRIPTION OF THE DRAWINGS

The FIGURE illustrates phasecontrast images before incubation and fully formed biofilms after 48h of incubation at 30° C.: (A) illustrates a phasecontrast image of a biofilm of *P. aeruginosa* ATCC 15442 before treatment; (B) illustrates a phasecontrast image of a biofilm of *P. aeruginosa* ATCC 15442 after treatment with a formulation of rhamnolipid (0.04%) and caprylic acid (0.01%) according to an embodiment of the present invention; (C) illustrates a phasecontrast image of a biofilm of *S. aureus* ATCC 9144 before treatment; (D) illustrates a phasecontrast image of a biofilm of *S. aureus* ATCC 9144 after treatment with a formulation of rhamnolipid (0.04%) and caprylic acid (0.01%) according to an embodiment of the present invention; (E) illustrates a phasecontrast image of a mixed culture biofilm of *P. aeruginosa* ATCC 15442/*S. aureus* ATCC 9144 before treatment; (F) illustrates a phasecontrast image of a mixed culture biofilm of *P. aeruginosa* ATCC 15442/*S. aureus* ATCC 9144 after treatment with a formulation of rhamnolipid (0.04%) and caprylic acid (0.01%) according to an embodiment of the present invention; (G) illustrates a phasecontrast image of a biofilm of *P. aeruginosa* ATCC 15442 before treatment; and (H) illustrates a phasecontrast image of a biofilm of *P. aeruginosa* ATCC 15442 after treatment with PBS 1X.

Mono-rhamnolipids have a single rhamnose sugar ring. The IUPAC Name is 3-[3-[(2R,3R,4R,5R,6S)-3,4,5-trihydroxy-6-methyloxan-2-yl]oxydecanoyloxy]decanoic acid.

Di-rhamnolipids have two rhamnose sugar rings. The IUPAC name is 3-[3-[4,5-dihydroxy-6-methyl-3-(3,4,5-trihydroxy-6-methyloxan-2-yl)oxyoxan-2-yl]oxydecanoyloxy]decanoic acid.

In the case of rhamnolipids, throughout this patent specification, the prefixes mono- and di- are used to indicate respectively to indicate mono-rhamnolipids (having a single rhamnose sugar ring) and di-rhamnolipids (having two rhamnose sugar rings) respectively. If abbreviations are used R1 is mono-rhamnolipid and R2 is di-rhamnolipid.

The mono-rhamnolipid may be L-rhamnosyl-β-hydroxydecanoyl-β-hydroxydecanoate (RhaC$_{10}$C$_{10}$ with a formula of C$_{26}$H$_{48}$O$_9$) produced by *P. aeruginosa*.

A typical di-rhamnolipid is L-rhamnosyl-L-rhamnosyl-β-hydroxydecanoyl-β-hydroxydecanoate (Rha2C$_{10}$C$_{10}$ with a formula of C$_{32}$H$_{58}$O$_{13}$).

In practice a variety of other minor components with different alkyl chain length combinations, depending upon carbon source and bacterial strain, exist in combination with the above more common rhamnolipids. The ratio of mono-rhamnolipid and di-rhamnolipid may be controlled by the production method. Some bacteria only produce mono-rhamnolipid, see U.S. Pat. No. 5,767,090: Example 1, some enzymes can convert mono-rhamnolipid to di-rhamnolipid.

The following rhamnolipids are sources of mono- and di-rhamnolipids encompassed within the invention (C12:1, C14:1 indicates fatty acyl chains with double bonds):

Rhamnolipids produced by *P. aeruginosa* (mono-rhamnolipids):

Rha-C$_8$-C$_{10}$, Rha-C$_{10}$-C$_8$, Rha-C$_{10}$-C$_{10}$, Rha-C$_{10}$-C$_{12}$, Rha-C$_{10}$-C$_{12:1}$, Rha-C$_{12}$-C$_{10}$, Rha-C$_{12:1}$-C$_{10}$.

Rhamnolipids produced by *P. chlororaphis* (mono-rhamnolipids only):

Rha-C$_{10}$-C$_8$, Rha-C$_{10}$-C$_{10}$, Rha-C$_{12}$-C$_{10}$, Rha-C$_{12:1}$-C$_{10}$, Rha-C$_{12}$-C$_{12}$, Rha-C$_{12:1}$-C$_{12}$, Rha-C$_{14}$-C$_{10}$, Rha-C$_{14:1}$-C$_{10}$.

Mono-rhamnolipids may also be produced from *P. putida* by introduction of genes rhlA and rhlB from *Psuedomonas aeruginosa* [Cha et al. in Bioresour Technol. 2008. 99(7):2192-9]

Rhamnolipids produced by *P. aeruginosa* (di-rhamnolipids):

Rha-Rha-C$_8$-C$_{10}$, Rha-Rha-C$_8$-C$_{12:1}$, Rha-Rha-C$_{10}$-C$_8$, Rha-Rha-C$_{10}$-C$_{10}$, Rha-Rha-C$_{10}$-C$_{12:13}$ Rha-Rha-C$_{10}$-C$_{12}$, Rha-Rha-C$_{12}$-C$_{10}$, Rha-Rha-C$_{12:1}$-C$_{12}$, Rha-Rha-C$_{10}$-C$_{14:1}$

Rhamnolipids produced by *Burkholdera pseudomallei* (di-rhamnolipids only):

Rha-Rha-C$_{14}$-C$_{14}$.

Rhamnolipids produced by *Burkholdera* (*Pseudomonas*) *plantarii* (di-rhamnolipids only):

Rha-Rha-C$_{14}$-C$_{14}$.

Rhamnolipids produced by *P. aeruginosa* which are initially unidentified as either mono- or di-rhamnolipids:

C$_8$-C$_8$, C$_8$-C$_{10}$, C$_{10}$-C$_8$, C$_8$-C$_{12:1}$, C$_{12:1}$-C$_8$, C$_{10}$-C$_{10}$, C$_{12}$-C$_{10}$, C$_{12:1}$-C$_{10}$, C$_{12}$-C$_{12}$, C$_{12:1}$-C$_{12}$, C$_{14}$-C$_{10}$, C$_{14:1}$-C$_{10}$, C$_{14}$-C$_{14}$.

Preferably, the rhamnolipid comprises at least 20 wt % di-rhamnolipid preferably 50 wt % di-rhamnolipid, more preferably 60 wt %, even more preferably 75 wt % and most preferably at least 90 wt % di-rhamnolipid.

The composition according to the invention can be used as bactericidal raw material such that the user e.g. consumer dilutes in a further composition or the composition may be a consumer product the application of which is intended to provide bactericidal effect to a substrate or even as a preservative within the consumer composition.

Preferably the cell membrane disrupter comprises an acid, more preferably an organic acid.

Preferred organic acids for use herein include carboxylic acids and mixtures thereof.

Preferred carboxylic acids include aliphatic, cycloaliphatic or aromatic mono-, di-, tri- or polycarboxylic acids or combinations/mixtures thereof. Polycarboxylic acids preferably contain 2 to 10 carbon atoms, more preferably 3 to 6 carbon atoms in the molecule. Hydroxycarboxylic acids may also be used.

The organic acid may be a fatty acid.

Preferred carboxylic acids include caprylic acid, propionic acid, azelaic acid, caproic acid, hydroxybenzoic acid, salicylic acid, malic acid, maleic acid, fumaric acid, succinic acid, glutaric acid, adipic acid, citric acid tartaric acid, and mixtures thereof.

Commercially available mixtures comprise 30-35% adipic acid, 45-50% glutaric acid and 10-18% succinic acid. Such a mixture is available as SOKALAN DCS ex BASF. Another suitable mixture is available as RADIMIX ex Radici.

Preferably the cell membrane disruptor is present in the range 0.01-10 wt. % of the formulation. More preferably the cell membrane is present in the range 5-10 wt. %.

Preferably, the composition is a home care and personal product.

Preferred home care products include laundry detergent/cleaning compositions, laundry conditioning composition compositions, and hard surface cleaners such as hand and machine dish washing compositions, kitchen and bathroom cleaners. Hard surfaces include kitchen and bathroom surfaces, cutlery, crockery etc.

Personal care compositions include shampoos, hair conditioners, deodorants, skin cleansing compositions and oral care products such as toothpastes and mouthwashes.

The following are non limiting embodiments of the invention, included by way of example only.

EXAMPLE 1

The following data illustrates the bacteriostat efficacy of a composition comprising a rhamnolipid and a cell membrane disruptor, caprylic acid.

Materials and Methods

Microorganisms and Culture Conditions

*P. aeruginosa* ATCC 15442 and *Staphylococcus aureus* ATCC 9144, were maintained in nutrient broth plus 20% glycerol at −20° C. Bacterial growth from a nutrient agar slant incubated for 24 h at 30° C. was used to obtain a bacterial suspension with an optical density at 570 nm adjusted to give 108 cfu/mL.

Rhamnolipid Characteristics

Rhamnolipid containing 10% (w/v) mono-rhamnolipid ($C_{26}H_{48}O_9$, MW: 504, Critical Micelle Concentration: 20 mg/L M at neutral pH) and 10% (w/v) dirhamnolipid ($C_{32}H_{58}O_{13}$, MW: 650, CMC: 1.5×10-4 30 mg/L at neutral pH) was obtained separated from a sample obtained from Jeneil Biosurfactant Co. (Saukville, Wis.).

Cell Membrane Disruptor: Caprylic Acid

Caprylic Acid (CAS RN 0124-07-2) was obtained from Sigma Aldrich (Catalogue number C2875) as >99% purity.

The Mono- and di-rhamnolipid was separated from the sample obtained from Jeneil using the protocol below and the individual R1/R2 fractions obtained were used to produce the 10% rhamnolipid solution mentioned above A quantified amount of JBR425 was acidified to pH 3 using 12M HCl and placed in a refrigerator overnight. The supernatant was then extracted three times using a 2:1 mixture of Chloroform and Ethanol. The solvent was then removed by rotary evaporation and the isolated rhamnolipid mixture was then re-dissolved in methanol.

The process of separating and characterising the mixture was carried out using an HPLC connected to an Ion Trap Electrospray ionisation Mass Spectrometer. The mode of ionisation was in negative mode with a scanning range of 50-1200 Da. The column used to separate was a Phenomenex luna C18 250×4.6 mm 5 µm column. The mobile phase: water (mobile phase A) and acetonitrile (mobile phase B) were used to separate via a gradient of 60:40 (A:B) changing to 30:70 (A:B) over 30 minutes. The system was then held for 5 minutes before returning to the start conditions all at a flow rate of 0.5 ml/min. The injection volume was 10 µl.

TABLE 1

Analysis of JBR425 via HPLC/MS

| Rhamnolipid Congeners | m/z | % |
|---|---|---|
| Di - C10-C8 | 621 | 1.6 |
| Di - C8-C10 | 621 | 1.3 |
| Di - C10-C10 | 649 | 67.4 |
| Di - C10-C12:1 | 675 | 0.78 |
| Di - C12:1-C10 | 675 | 0.016 |
| Di - C10-C12 | 677 | 3.18 |
| Di - C12-C10 | 677 | 1.12 |

TABLE 1-continued

Analysis of JBR425 via HPLC/MS

| Rhamnolipid Congeners | m/z | % |
|---|---|---|
| Mono - C10-C8 | 475 | 0.63 |
| Mono - C8-C10 | 475 | 0.47 |
| Mono C10-C10 | 503 | 21.6 |
| Mono - C10-C12:1 | 529 | 0.69 |
| Mono -C12:1-C10 | 529 | 0.014 |
| Mono C10-C12 | 531 | 1.12 |
| Mono -C12-C10 | 531 | 0.023 |

Biofilm Growth on the BioFlux Flowthrough Device.

To analyze biofilm formation under flow conditions, the BioFlux 200 system (Fluxion Biosciences Inc., South San Francisco, Calif.) was used which allows automated image acquisition within specialized multi-well plates. To grow biofilms, the microfluidic channels (depth, 75 µm; width, 350 µm) were primed with TSB (50%) at 10.0 dyn/cm2. Channels were seeded with 107 CFU from an overnight culture of *P. aeruginosa* ATCC 15442, *Staphylococcus aureus* ATCC 9144 and a mixed culture of both. The plate was then incubated at 30° C. for 48 h to allow cells to adhere. After biofilms had formed, planktonic cells were removed, and PBS 1× (as control) and different treatments were added to the input wells at a flow rate of 279 µL/h for 30 min. The results were recorded with a microscope Evon (10×) (17% Light)

Results

Biofilm Disruption of *Pseudomonas aeruginosa* ATCC 15442, *Staphylococcus aureus* ATCC 9144 and a Mixed Culture Using Rhamnolipids and Caprylic Acid.

The effect of rhamnolipid together with caprylic acid on pre-formed biofilms by *Pseudomonas aeruginosa* ATCC 15442, *Staphylococcus aureus* ATCC 9144 and a mixed culture was determined under Bioflux flowthrough conditions. The disruption produced by the combination of caprylic acid together with rhamnolipids was confirmed. All isolates developed biofilms over 48 h. However, there was considerable variability in all cases in terms of spread around of the microfluidic channel. *Pseudomonas aeruginosa* biofilms and the mixed culture were well-formed (FIGS. (A), (E) and (G)) under flow conditions, however the biofilms formed by *Staphylococcus aureus* ATCC 9144 (FIG. (C)) were not as thick, but good enough to be considered a multicellular community that represented a fundamentally different physiological state compared to free-living planktonic bacteria.

After 48 h all the plates were rinsed with PBS 1×, and the treatments with the combination of rhamnolipids (0.04% v/v) and caprylic acid (0.01% v/v) were applied for 30 minutes, after which period more than the 90% of the biofilms were disrupted. It is interesting to note that the way that the Gram-positive and Gram-Negative microorganisms respond to the combination between rhamnolipids and caprylic acid varied, suggesting a possible synergy between them compared to the results when the components are applied individually (data not shown). The results are illustrated in the Figure which shows Biofilm formation and disruption in a BioFlux channel. The images are phasecontrast images and show fully formed biofilms after 48 h of incubation at 30° C., and the images were recorded with a microscope Evon (10×) (17% Light) as follows (A) *P. aeruginosa* ATCC 15442 biofilm before treatment.

(B) *P. aeruginosa* ATCC 15442 (A) after treatment with Rhamnolipid (0.04%) and Caprylic acid (0.01%).

(C) *S. aureus* ATCC 9144 before treatment.

(D) *S. aureus* ATCC 9144 (C) after treatment with Rhamnolipid (0.04%) and Caprylic acid (0.01%).

(E) Mixed Culture (*P. aeruginosa* ATCC 15442/*S. aureus* ATCC 9144) before treatment.

(F) Mixed Culture (E) after treatment with Rhamnolipid (0.04%) and Caprylic acid (0.01%).

(G) *P. aeruginosa* ATCC 15442 before treatment.

(H) *P. aeruginosa* ATCC 15442 (G) after treatment with PBS 1×.

The invention claimed is:

1. An antimicrobial composition comprising:
   a rhamnolipid; and
   a cell membrane disruptor comprising caprylic acid,
   wherein:
      the rhamnolipid comprises at least 50 wt % di-rhamnolipid; and
      the cell membrane disruptor is present in the range of 0.01-10 wt % of the composition.

2. The composition according to claim 1, wherein the composition further includes a synthetic surfactant.

3. The composition according to claim 1, wherein the rhamnolipid is present at 1 wt %-95 wt % of the total surfactant.

4. The composition according to claim 1, wherein the composition is a homecare or personal care composition.

5. The composition according to claim 4, wherein the composition is a personal care composition selected from the group consisting of a shampoo, conditioner, deodorant, skin cleansing composition, and antiperspirant.

6. The composition according to claim 4, wherein the composition is a homecare composition selected from the group consisting of a laundry composition and a hard surface cleaner.

7. The composition according to claim 3, wherein the rhamnolipid is present at 10 wt %-70 wt % of the total surfactant.

8. The composition according to claim 1, wherein the cell membrane disruptor is present in the range from 0.01-5 wt % of the composition.

9. The composition according to claim 1, wherein the cell membrane disruptor further comprises a carboxylic acid selected from the group consisting of azelaic acid, caproic acid, malic acid, maleic acid, fumaric acid, succinic acid, glutaric acid, adipic acid, tartaric acid, and mixtures thereof.

* * * * *